(12) United States Patent
Batiste

(10) Patent No.: US 9,039,758 B2
(45) Date of Patent: May 26, 2015

(54) BYPASS VASCULAR GRAFT

(76) Inventor: Stanley Batiste, Las Vegas, NV (US)

( * ) Notice: Subject to any disclaimer, the term of this patent is extended or adjusted under 35 U.S.C. 154(b) by 1292 days.

(21) Appl. No.: 11/977,953

(22) Filed: Oct. 26, 2007

(65) Prior Publication Data

US 2008/0140183 A1    Jun. 12, 2008

Related U.S. Application Data

(60) Provisional application No. 60/873,788, filed on Dec. 7, 2006.

(51) Int. Cl.
*A61F 2/06* (2013.01)

(52) U.S. Cl.
CPC .. *A61F 2/064* (2013.01); *A61F 2/06* (2013.01)

(58) Field of Classification Search
CPC ......................................................... A61F 2/06
USPC ............. 623/1.1, 1.13, 1.24, 1.25, 1.27, 1.31, 623/1.11, 1.15, 1.35; 604/8; 600/36; 128/898
See application file for complete search history.

(56) References Cited

U.S. PATENT DOCUMENTS

| | | | | |
|---|---|---|---|---|
| 5,197,976 | A  * | 3/1993 | Herweck et al. | 623/1.27 |
| 5,662,711 | A  * | 9/1997 | Douglas | 604/9 |
| 6,338,724 | B1 * | 1/2002 | Dossa | 604/8 |
| 6,589,278 | B1 * | 7/2003 | Harris et al. | 623/1.31 |
| 7,105,020 | B2 * | 9/2006 | Greenberg et al. | 623/1.35 |
| 7,128,750 | B1 * | 10/2006 | Stergiopulos | 606/158 |
| 2008/0161839 | A1* | 7/2008 | Shalev | 606/153 |

* cited by examiner

*Primary Examiner* — Thomas J Sweet
*Assistant Examiner* — Matthew Schall
(74) *Attorney, Agent, or Firm* — Weide & Miller, Ltd.

(57) ABSTRACT

A vascular bypass graft having a primary member and a secondary member is disclosed. The secondary member extends from a distal second end of the primary member and has a common fluid pathway there between. The secondary member may have a flared or diffused proximal first end that facilitates low pressure fluid return and may be integrally formed with the primary member. An adjustable or fixed stenosis is provided in the secondary member which allows the fluid flow through the vascular bypass graft to be modified. The stenosis may be adjusted either manually or by way of a controller. The primary member is surgically connected to a patient's vascular system to provide an alternate route for blood flow around a vascular occlusion. The secondary member is surgically connected to another point in the vascular system to allow continuous circulation of blood through the graft thereby preventing clotting and graft failure.

23 Claims, 5 Drawing Sheets

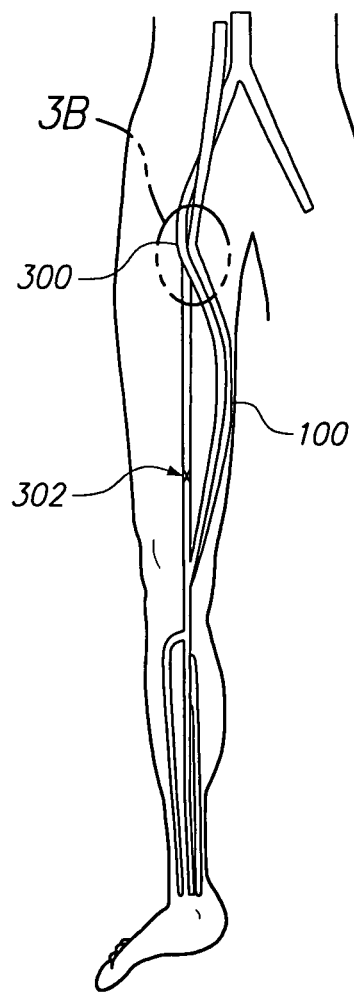
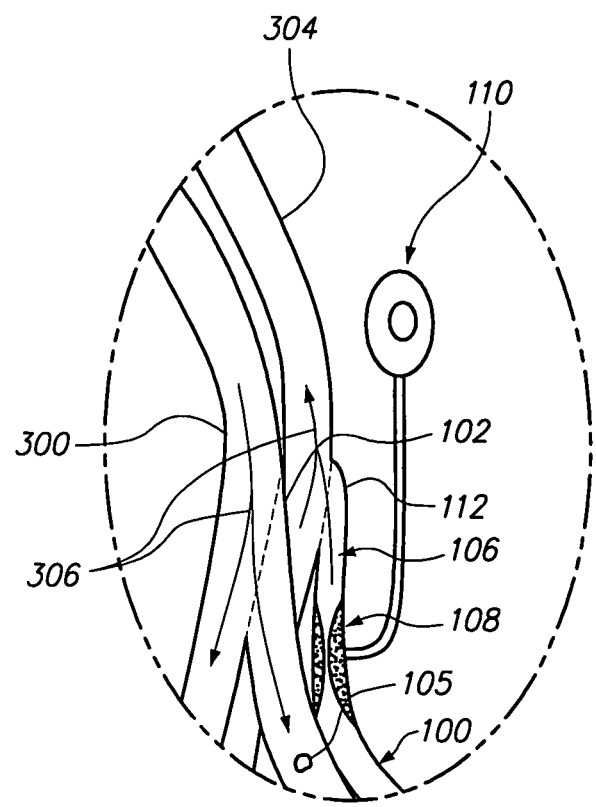
FIG. 3A
FIG. 3B

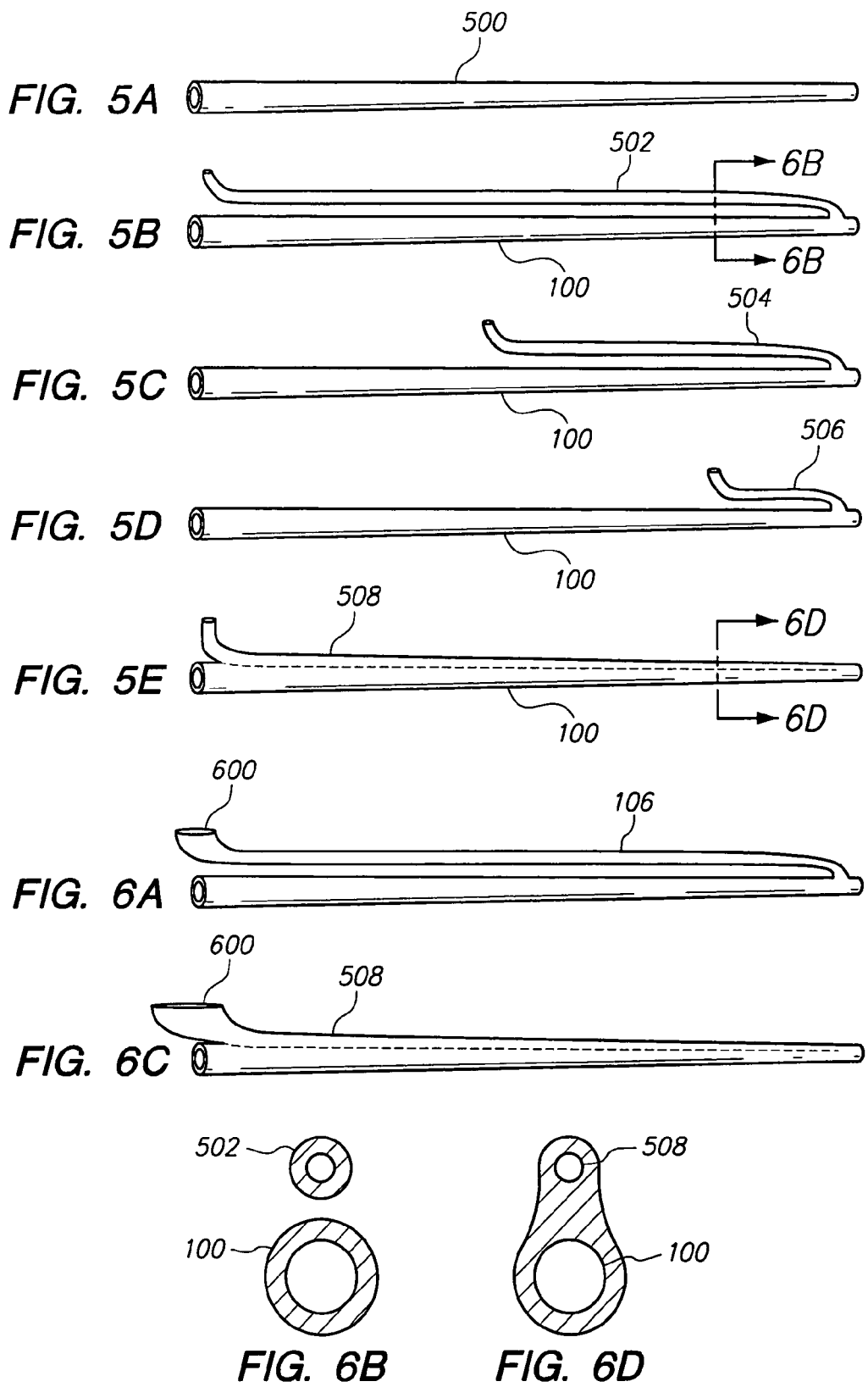

BYPASS VASCULAR GRAFT

CROSS-REFERENCE TO RELATED APPLICATIONS

This application claims priority to U.S. Provisional Patent Application No. 60/873,788 filed on Dec. 7, 2006 titled IMPROVED BYPASS VASCULAR GRAFT.

BACKGROUND OF THE INVENTION

1. Field of the Invention

The present invention relates to vascular bypass grafts and, in particular, to surgically implanted grafts which increase blood flow and reduce clotting.

2. Related Art

Vascular disease is a leading cause of morbidity and mortality in the United States and throughout the world. The causes of vascular disease include diabetes, hypertension, renal failure, and smoking as well as many other etiologies. Vascular disease can affect any blood vessel in the body and commonly involves the coronary arteries, carotid arteries and the arteries of the lower extremities. The disease is caused by cholesterol, plaque, and calcium deposits which cause vascular wall thickening. Vascular wall thickening occludes the afflicted vessels by narrowing them, which reduces or in some cases, completely blocks blood flow.

Vascular disease is currently treated in several different ways. Patients may engage lifestyle changes, changes to diet and exercise, and medical therapies such as cholesterol lowering drugs. However, for some patients, these non-invasive treatments are insufficient and surgical or invasive intervention such as bypass surgery or angioplasty are necessary.

A patient undergoing bypass surgery has a bypass graft, surgically implanted. The bypass graft provides a substitute route for blood flow to bypass an occluded region. The bypass graft is a tube structure with two ends. One end attaches on one end before the region of vascular occlusion, and on the other end to the patient's vascular system downstream of the occlusion. In this manner, the bypass graft improves the patient's blood flow around the occlusion.

The majority of bypass grafts function well over time, however, in a significant number of patients the bypass grafts themselves become occluded. Where a bypass graft becomes occluded, the patient must undergo another surgery to place a second graft or to repair the original graft.

As a result, there is a need in the art for a bypass graft that can provide a route for blood flow while preventing occlusion which leads to graft failure. The description herein enables such a bypass graft as well as a method of implanting the bypass graft.

BRIEF SUMMARY OF THE INVENTION

A vascular bypass graft is disclosed which improves blood flow in an occluded region of a patient's vascular system by providing an alternate route for blood to flow. In one embodiment the vascular bypass graft has a primary graft member through which the blood flow is primarily directed, and an outflow limb or secondary graft member through which circulation of blood through the graft can be maintained to prevent clotting.

The circulation of blood through the secondary graft member has the advantage of maintaining a high blood flow rate in conditions where there would ordinarily be a low blood flow rate. The high flow rate prevents blood clots which would occlude the graft and lead to graft failure as often seen in known bypass grafts.

Generally, the graft utilizes an adjustable or fixed blood flow restrictor which is used in conjunction with the outflow limb member to control amount of blood circulation and pressure within the bypass graft. This allows the bypass graft to be customized to a particular patient and allows the flow rate to be changed as medical conditions or other factors dictate. In addition, the adjustable configurations of the invention allow changes to flow rate automatically and without further surgery.

In one embodiment, the primary graft member has openings on both its ends, one to allow the flow of blood into the vascular bypass graft and the other to allow the flow of blood to continue past an occlusion and back out to the vascular system. Near the end where blood flows back to the vascular system is attached the secondary graft member through which another flow of blood is circulated back to the vascular system. This circulation prevents clotting within the graft.

The primary and secondary graft members may be formed in various ways. In one embodiment they are integrally formed so as to share a single main body. In another embodiment the secondary member is flared out at the point it is attached to the vascular system. In yet another embodiment, the secondary graft member may include a stenosis restrictor which can control pressure and flow within the graft by reducing or even blocking the flow of blood through the secondary graft member.

The stenosis restrictor may be positioned adjacent to the point where the secondary member attaches to the vascular system and may be configured to set a fixed flow rate through the graft. Additionally, one or more embodiments may include a restrictor controller to control the stenosis restrictor's function. This controller may be connected to various pressure, flow rate, or other sensors so that it may better control the stenosis restrictor. The controller may function on its own in a closed-loop fashion or, in other embodiments, the controller may communicate with an external device wirelessly or by physical connection. This communication can serve multiple purposes including but not limited to control of the stenosis restrictor.

In one embodiment, the flow of blood through the graft may be controlled by continuously or periodically monitoring the characteristics of the fluid flow and pressure through the graft, determining the condition of the fluid flow through the graft using these characteristics, and then controlling the stenosis restrictor accordingly to adjust the fluid flow within the graft. In other embodiments the information used to adjust fluid flow may include other characteristics such as but not limited to the flow characteristics of the graft itself.

The graft may be surgically implanted by various methods. In one embodiment, the graft is implanted adjacent to a vascular occlusion in a manner that provides an alternate route for blood flow. This occurs by connecting the inflow end of the primary graft member to the vascular system upstream of the vascular occlusion, and connecting the other end to the vascular system downstream of the vascular occlusion. The secondary graft member is then connected to another point in the vascular system to allow for continuous circulation within the graft.

Further objects, features, and advantages of the present invention over the prior art will become apparent from the detailed description of the drawings which follows, when considered with the attached figures.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

FIG. 3A is a regional view of the proximal connections of the vascular bypass graft of FIG. 1.

FIG. 3B is an enlarged detail view of the proximal connections of the vascular bypass graft of FIG. 1.

FIGS. 5A through 5E illustrate a series of alternate embodiments of an vascular bypass graft.

FIG. 6A illustrates an alternate embodiment of an vascular bypass graft having a flared venous outflow limb.

FIG. 6B is a cross-sectional view of the alternate embodiment of FIG. 6A.

FIG. 6C illustrates an alternate embodiment of a vascular bypass graft having an integral flared venous outflow limb.

FIG. 6D is a cross-sectional view of the alternate embodiment of FIG. 6C.

DETAILED DESCRIPTION OF THE PREFERRED EMBODIMENTS

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

The primary reason for the formation of blood clots in a bypass graft is that the blood flow through the graft is of such low velocity that blood clotting mechanisms are triggered. Regions of low velocity blood flow are common in the body's smaller vessels such as veins and capillaries. Low velocity regions are also found in the transitions between larger vessels, such as arteries, to smaller ones, such as veins or capillaries because the reduction in size reduces flow capacity and thus blood flow velocity is also reduced. Thus, if a bypass graft is attached to a small vessel at its outflow end or in a region of low velocity blood flow, only a small amount of blood at low velocity flows through the graft creating circumstances where blood clots may form within the graft. This will cause occlusion of the graft and eventual graft failure.

In general, a vascular bypass graft which improves blood flow in occluded vascular regions and is itself resistant to occlusion by blood clots is disclosed. The vascular bypass graft disclosed herein has several advantages over known bypass grafts. It maintains a high blood flow velocity in conditions where there would otherwise be a low flow rate through the graft, such as where outflow from the distal vascular bypass graft end is low or reduced. Currently known grafts will not stay un-occluded in these conditions because the slow flow through the graft allows blood clots to develop and occlude the graft eventually rendering it non-functional.

Another advantage of the method and apparatus described herein is that the amount of return flow provided through the venous outflow limb is adjustable. In this way, the vascular bypass graft can be custom configured for a particular patient and/or medical application. One aspect of this adjustability is that it is non-invasive and thus allows modification of the amount of blood flow through the vascular bypass graft in response to the new medical conditions or other factors without the need for further surgery.

Figure 1:
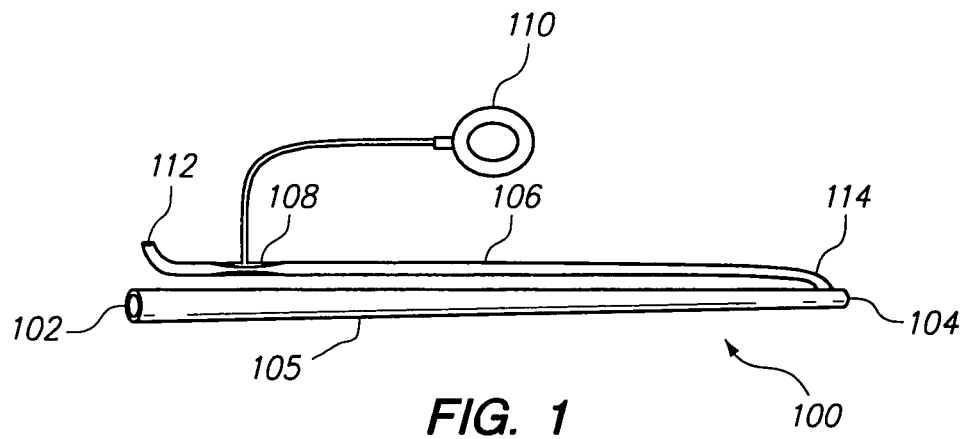
FIG. 1 illustrates an exemplary embodiment of a vascular bypass graft.

Referring now to the drawings, FIG. 1 illustrates an improved vascular bypass graft 100. The vascular bypass graft 100 has a primary member/graft 105, a proximal/first vascular bypass end 102, a distal/second vascular bypass end 104, a venous outflow limb 106, a stenosis restrictor 108, and an optional restrictor controller 110. The venous outflow limb 106 or secondary member has a proximal/first venous end 112 and a distal/second venous end 114. The distal venous end 114 attaches to or is integrally formed adjacent to the distal vascular bypass end 104 such that a flow path is provided that facilitates fluid transmission from the primary graft 105 to the venous outflow limb 106. The venous outflow limb 106 or secondary member extends from a wall of the primary member at the distal/second end 104 of the primary member as shown in FIG. 1 to form a fluid pathway between the primary member 105 and the venous outflow limb 106. The vascular bypass graft 100 or any portion thereof can be made in any length to accommodate the need for various vascular systems.

The primary graft 105 is generally a flexible hollow elongate member comprising structure and dimensional configurations to facilitate fluid transmission from the proximal vascular bypass end 102 to the distal vascular bypass end 104. The venous outflow limb 106 is generally a flexible hollow elongate member structured and dimensionally configured to facilitate fluid transmission from the distal venous end 114 to the proximal venous end 112. In one embodiment, the primary graft 105 and venous outflow limb 106 are fabricated from a material that is suitable for surgical implantation into a living organism. The material should be selected for compatibility with living tissue. Such materials include but are not limited to prosthetic polytetraflouroethylene (PTFE) and polyethylene tetraphthalate (Dacron).

In one embodiment, when implanted, the vascular bypass graft 100 is attached to a patient's vascular system at the proximal vascular bypass end 102, the distal vascular bypass end 104, and the proximal venous end 112. In one embodiment, the vascular bypass graft is implanted such that blood flows through the primary graft 105 from the proximal vascular bypass end 102 to the distal vascular bypass end 104. The proximal venous end 112 of the venous outflow limb 106 may be attached to a blood vessel of lower pressure. This attachment of the proximal venous end 112 to a blood vessel of lower pressure ensures that at least a portion of blood in the primary graft 105 flows through the venous outflow limb 106 because fluids, including blood, will naturally flow to a region of lower relative pressure.

The venous outflow limb 106 allows the primary graft 105 to maintain blood flow velocity sufficient to prevent clotting even when the flow velocity would ordinarily be low due to minimal outflow through the distal vascular bypass end 104. Blood flow travels through the primary graft 105 from the proximate vascular bypass end 102 to the distal vascular bypass end 104 with at least a portion of the blood flow diverted through the venous outflow limb 106. This portion of diverted blood flow allows the blood to circulate through the vascular bypass graft 100 at a flow velocity sufficient to prevent clotting even where the patient's vascular system at the distal vascular bypass end 104 has a low blood flow capacity. Thus, the patient's vascular system at the distal vascular bypass end 104 receives its necessary blood flow while the excess blood flow is circulated through the venous outflow limb 106 to a blood vessel of lower pressure to prevent clotting within the vascular bypass graft 100.

The stenosis restrictor 108 controls the amount of blood flow through the venous outflow limb 106 by restricting blood flow through the venous outflow limb 106. The stenosis restrictor 108 can completely restrict (i.e. block) blood flow as well. This control is desirable because it allows the vascular bypass graft 100 to be configured to the needs of each particular patient at a particular time. More specifically, the stenosis restrictor 108 can increase or decrease blood pressure at the distal vascular bypass end by increasing or decreasing the amount of blood flowing through the venous outflow limb 106. Thus, the stenosis restrictor 108 could decrease blood flow through the venous outflow limb to increase blood pressure, for example, to outer extremities or anytime the body requires it such as during physical activity. Conversely, the stenosis restrictor 108 could increase blood flow through the venous outflow limb to decrease blood pressure at the distal vascular bypass end 104 and increase anti-clotting circulation through the vascular bypass graft 100 when such increased blood pressure is not necessary.

In one embodiment, a desired flow condition provides sufficient flow through the primary graft 105 to prevent clotting while still maintaining sufficient pressure at the distal vascular bypass end 104. By selecting the proper stenosis restrictor 108 setting, the pressure and flow rate may be optimized.

The stenosis restrictor 108 may comprise various configurations, devices, or systems that restrict blood flow to achieve operation as described herein including but not limited to balloon or other inflatable devices or other pneumatic or hydraulic systems. In addition, the stenosis restrictor 108 may operate in conjunction with a restrictor controller 110 to variably control the amount of blood flow restriction.

In one embodiment the stenosis restrictor 108 comprises a balloon. In this embodiment, the restrictor controller 110 comprises a pneumatic or hydraulic device for inflating and deflating the balloon to thereby adjust the amount of blood flow restriction. The restrictor controller 110 as a pneumatic or hydraulic device may be configured as a gas or liquid reservoir connected to the stenosis restrictor 108. The amount of blood flow restriction can then be varied by altering the volumetric capacity of the restrictor controller 110 to which the stenosis restrictor 108 is linked. The degree to which the stenosis restrictor 108 restricts blood flow through the venous outflow limb 106 may be substantially proportional and inverse to the volumetric capacity of the restrictor controller 110 of this embodiment.

Figure 2A:
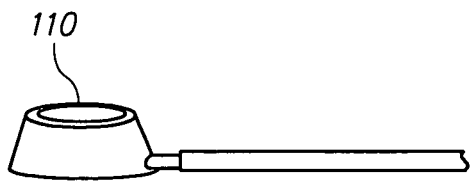
FIG. 2A illustrates a reservoir for a stenosis restrictor of the vascular bypass graft of FIG. 1.
Figure 2B:
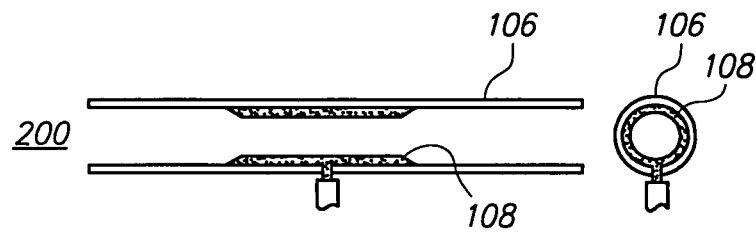
FIG. 2B illustrates a cross-sectional view of a deflated stenosis restrictor of FIG. 1.
Figure 2C:
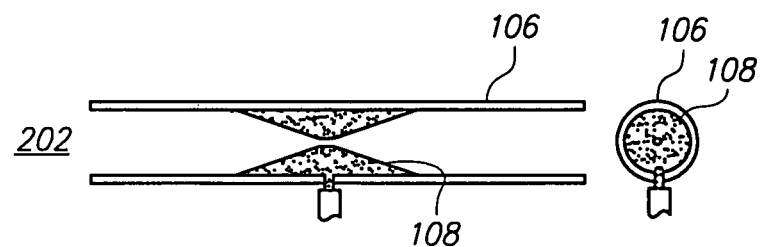
FIG. 2C illustrates a cross-sectional view of an inflated stenosis restrictor of FIG. 1.

The stenosis restrictor 108 and restrictor controller 110 are illustrated in greater detail in FIGS. 2A through 2C. In FIGS. 2B and 2C the stenosis restrictor 108 is shown in both a longitudinal cross-section and a transverse cross-section. Additionally, the stenosis restrictor 108 is depicted in a first deflated state 200 in FIG. 2B and a second inflated state 202 in FIG. 2C. As shown in FIG. 2B, the stenosis restrictor 108 is deflated and provides little resistance to fluid flow within the venous outflow limb 106 thus reducing fluid pressure within the primary graft 105. Conversely, in FIG. 2C, the stenosis restrictor 108 is inflated providing increased resistance to fluid flow within the venous outflow limb 106 thus increasing the overall fluid pressure within the vascular bypass graft.

Reference is now made to FIGS. 3A and 3B which illustrate an embodiment of the vascular bypass graft 100 attached to a patient's vascular system. The proximate vascular bypass end 102 of the vascular bypass graft 100 is attached to a patient's artery 300 at a proximate end located upstream from the vascular occlusion 302. This results in blood flow 306 being diverted into the vascular bypass graft 100 from the artery 300. The proximate venous end 112 is attached to a patient's blood vessel 304 of lower pressure, to permit blood flowing through the venous outflow limb 106 to return to the patient's vascular system.

Figure 4A:
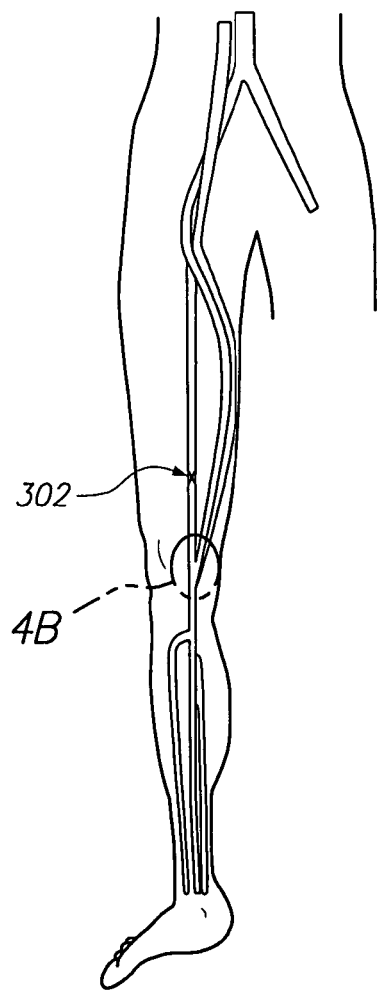
FIG. 4A is a regional view of the distal connections of the vascular bypass graft of FIG. 1.
Figure 4B:
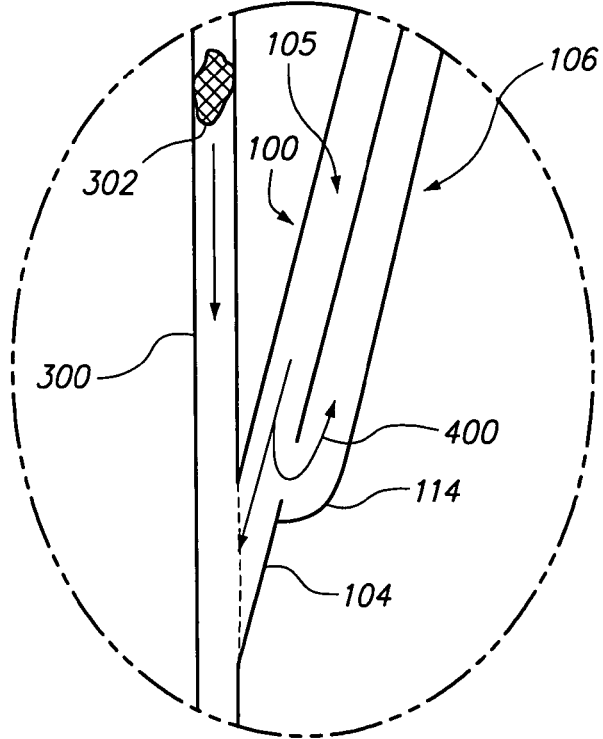
FIG. 4B is an enlarged detail view of the distal connections of the vascular bypass graft of FIG. 1.

FIGS. 4A and 4B illustrate the distal end of the vascular bypass graft 100 attaching to a patient's vascular system. The distal vascular bypass end 104 of the vascular bypass graft 100 is attached to a patient's artery 300 at a distal end located downstream from the vascular occlusion 302. The blood flow that was diverted into the vascular bypass graft 100 from the artery 300 as described above reenters the artery at a location beyond the vascular occlusion thus bypassing said vascular occlusion 302. As seen in FIG. 4B, a portion of the blood flow 400 through the vascular bypass graft's 100 primary graft 105 is diverted into the venous outflow limb 106 through the distal venous end 114 for subsequent return into the patient's vascular system by way of blood vessel 304 as shown in FIG. 3B.

It should be noted that the vascular bypass graft 100 as shown in FIGS. 3A, 3B, 4A, and 4B is shown in a particular vascular configuration. However, the vascular bypass graft 100 is designed to be utilized in any other suitable vascular system including but not limited to the upper extremity, the coronary arterial system and the abdominal, or pelvic vascular system.

Several variations of the vascular bypass graft 100 are shown in FIGS. 5B through 5E in comparison to a known standard bypass graft 500 as shown in FIG. 5A. The design of the venous outflow limb may take on various configurations including the side-by-side configuration shown in FIGS. 5B through 5D and cross-section FIG. 6B. In another embodiment, the vascular bypass graft 100 has a unitary construction with the venous outflow limb 106 being integrally formed with the vascular bypass graft 100 as shown in FIGS. 5E, 6A, and cross-section FIG. 6D. In the embodiment shown in FIG. 5B, the vascular bypass graft 100 comprises a long venous outflow limb 502. In another embodiment, the venous outflow limb may be a medium length venous outflow limb 504 as shown in FIG. 5C. In yet another embodiment, a short length venous outflow limb 506 may be configured with the vascular bypass graft 100 as shown in FIG. 5D.

It is contemplated that the various lengths of the venous outflow limbs are selected and implemented as required by the medical circumstances. For example, in one patient, the distal vascular bypass end may be located very close to a patient's vein and a short venous outflow limb 506 would facilitate connection of the venous outflow limb to the native vein in the most efficient manner. In contrast, the distal vascular bypass end may be located far away from a patient's native vein and the use of a long venous outflow limb 502 would be necessary. It is further contemplated that there are many variations with respect to the length of the venous outflow limb and other configurations are possible within the scope of the invention disclosed herein.

In one embodiment, the vascular bypass graft, including its primary graft portion and its venous outflow limb portion, are adjustable, separately or as a whole, such as by a cut-to-length fit during surgery to specially fit the vascular bypass graft to a particular patient.

FIG. 5E shows the embodiment where a venous outflow limb 508 is integrally formed with the vascular bypass graft

100. This integral venous outflow limb 508 makes the vascular bypass graft 100 easier to surgically place because there is primarily only one member to manipulate during the installation of the graft. By combining this venous outflow limb 508 with the primary structure of the vascular bypass graft 100 tangling or damage to this venous outflow limb 508 during surgery is reduced. As with the other embodiments, this venous outflow limb 508 can be made any length, independent of the length of the vascular bypass graft 100. The length of this venous outflow limb 508 also being dependant upon the distance required to extend to the best outflow attachment blood vessel.

In another embodiment, shown in FIGS. 6A and 6C, the venous outflow limb is configured with a flared proximate venous end 600. The flared proximate venous end 600 functions as a fluid diffuser that reduces the exit pressure of blood leaving the proximate venous end prior to re-entry into the patient's vascular system. As a result, the blood flow entering the patient's blood vessel is at a substantially similar pressure which reduces chances of blood clotting, and potential damage to the vascular walls at the re-entry blood vessel. A high pressure differential at the proximate venous end could result in repeated expansion and contraction of the re-entry blood vessel which in turn leads to scarring and thus narrowing of such blood vessel.

Additional embodiments may provide various means for adjusting or controlling the restrictor controller and/or the stenosis restrictor, including various pumps, valves, and devices for adjusting the stenosis restrictor or any other device, which may be dependent on the type of restrictor used. If a balloon-type stenosis restrictor is used, then a deflating/inflating device may be used to control the restriction on blood flow.

Figure 7A:
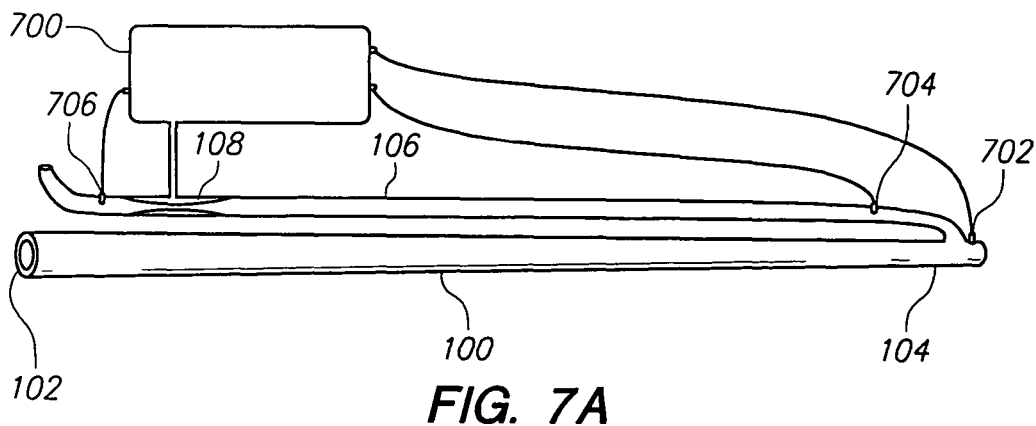
FIG. 7A illustrates an alternate embodiment of a vascular bypass graft having a controller.

In the embodiment shown in FIG. 7A, a controller 700, which may be electrical, mechanical, or a combination of both, is utilized to control the stenosis restrictor 108. The controller 700 can operate in conjunction with various combinations of graft output sensors 702, venous limb high pressure/flow sensors 704, or venous limb low pressure/flow sensors 706.

These sensors monitor one or more fluid dynamic parameters within the vascular bypass graft and provide this information to the controller 700 via electrical, optical, mechanical or other signaling. Fluid dynamic parameters are data relating to the movement of fluid within the vascular bypass graft such as but not limited to blood flow rate, pressure, or both. Fluid dynamic parameters may also include characteristics of the vascular bypass graft itself such as but not limited to the length and volumetric capacity of various sections of the vascular bypass graft.

Data comprising fluid dynamic parameters may be collected from the sensors in a variety of ways. In one embodiment, some or all the sensors are activated by the controller 700 when the controller requires or requests sensor information. However, in other embodiments, the sensors may continuously provide sensor information which the controller 700 may periodically, continuously, or at any other time collect. The controller may be operatively coupled to the stenosis. The term operatively coupled is defined to mean connected to or in communication with, such as by mechanical, physical electrical, pneumatic, magnetic, radio, or any other means.

Figure 7B:
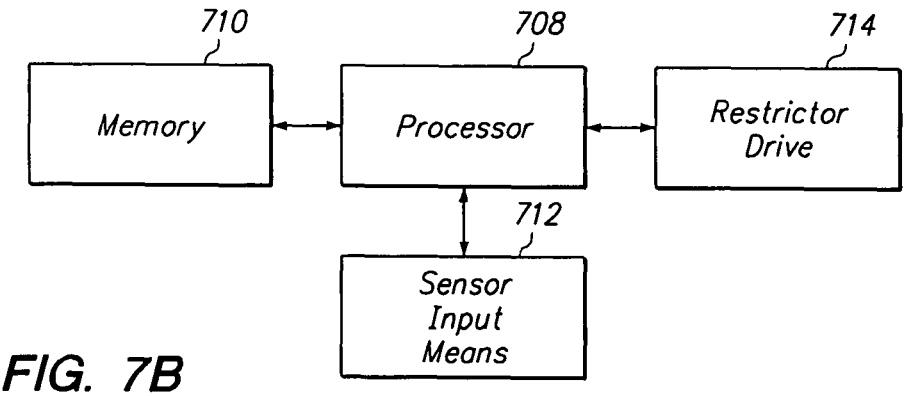
FIG. 7B is a block diagram of an exemplary embodiment for a closed-loop feedback controller of FIG. 7A.

FIG. 7B illustrates internal components for one embodiment of the controller 700. In this embodiment, the controller 700 has a processor 708 with memory 710 for storing machine executable code and sensor information. The machine executable code includes one or more sets of instructions which are interpreted or executed by the processor 708 to accomplish a desired result. In one or more embodiments, the machine executable code may instruct the processor 708 to collect sensor information, perform calculations upon or process the sensor information, and provide an output. This output may be used to control a restrictor driver 714 which controls the stenosis restrictor. The processor 708 may execute or the machine executable code may instruct the processor to use the memory 710 to store and/or retrieve data including but not limited to sensor information, intermediate or final outputs, or additional machine executable code. Communication between the internal components of the controller 700 may be bi-directional.

In one or more embodiments, the processor 708 may base its output or commands to the restrictor driver 714 on a plurality of sensor information collected through sensors connected to a sensor input 712. The controller 700 may be programmed to manually, periodically, or continuously monitor and adjust the performance of the vascular bypass graft based on fluid dynamic parameters such as but not limited to pressure or flow rate or both collected from various sources and sensors. The processor 708 may then adjust the stenosis restrictor accordingly.

For example, the vascular bypass graft 100 illustrated in FIG. 7A may be fitted with one or more of a graft output sensor 702, a venous limb high pressure/flow sensor 704 and/or a venous limb low pressure/flow sensor 706. The information from these sensors is communicated to the controller 700 to form a to closed-loop feedback control system for dynamic adjustment stenosis, which in turn controls the flow through the outflow limb, which in turn controls the flow through the vascular bypass graft 100. It is contemplated that the invention may be practiced with additional or fewer sensors 706 depending on the degree of flow control needed for a particular application.

Figure 7C:
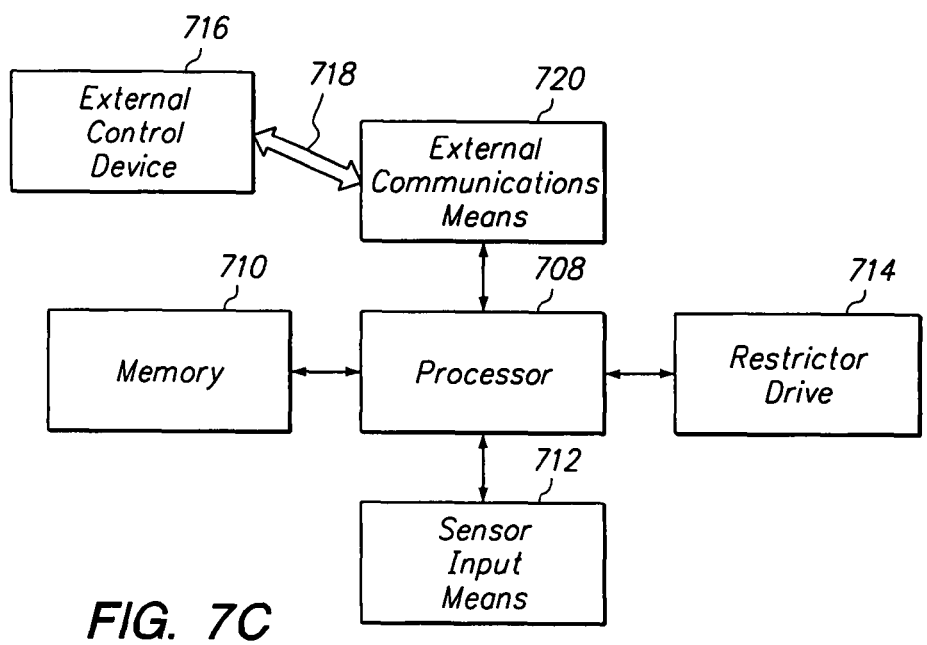
FIG. 7C is a block diagram of an exemplary embodiment for an open-loop feedback controller of FIG. 7A.

In another embodiment shown in FIG. 7C, the controller 700 is configured as an open-loop control system. In this variation, the processor 708 may communicate with an external control device 716. In this embodiment, the processor 708 may receive information from its sensor input 712 and then send the information to an external communication device 720 which transmits this information to an external control device 716. The processor 708 may also process the information prior to sending it to the external communication device 720.

In one embodiment, the external control device 716 may have a similar internal makeup as the controller 700. For example, the external control device 716 may comprise a processor, memory, external communication device, and sensor input. Thus, the external control device 716 may receive information from sensors, other devices, or other sources. When operating, the external control device 716 may perform some or all of the processing ordinarily done by the controller's 700 processor 708 or may supplement the processed output of the processor 708 through bi-directional communication with the processor 708. In addition, the external control device 716 may perform diagnostics on the controller 700, or record and/or relay information it receives to medical personnel for treatment purposes. In one or more embodiments the external control device 716 may be a computer.

The transmission of information can be a bi-directional communication link 718 with the external control device 716 such as by way of wireless connection such as radio transmission, microwave radio transmission (telemetry), and radio frequency identification methods. Alternately, the bi-directional communication link 718 may be effectuated by a direct connection with the external control device 716 such as by an externally accessible electro-mechanical connector.

Once the information is received by the external control device 716, the information may be evaluated and data may be transmitted back to the processor 708 via the bi-directional communication link 718. In one embodiment, the data causes processor 708 to signal the restrictor driver 714 to adjust the stenosis restrictor as necessary to achieve the desired flow rate and pressure. However, the processor 708 may further process the data prior to signaling the restrictor driver 714.

The above embodiment provides a bypass graft flow control system that may continuously or periodically monitor and adjust the flow rate through the vascular bypass graft and venous outflow limb in real-time. In this embodiment, the controller monitors the flow rates in the graft and adjusts the magnitude of the stenosis restrictor to thereby maintain or modulate the flow rate which in turn will reduce clotting.

It is also contemplated that the flow through the vascular bypass graft may be controlled in a time-variant manner. The controller may be configured to selectively open and close, to any degree, the stenosis restrictor at predetermined time intervals to purge or clear the vascular bypass graft of lingering low velocity blood flow thereby reducing or inhibiting blood clots. Additionally, alternative embodiments may purge or clear the vascular bypass graft whenever a sufficiently low velocity blood flow is detected.

It is contemplated that another variation of the vascular bypass graft disclosed herein is configured with a fixed stenosis restriction. In this variation, the blood flow restriction in the venous outflow limb is non-adjustable. Thus, the proper flow rate through the vascular bypass graft would be determined and configured during its manufacture or when placed in a patient. Multiple different vascular bypass grafts of differing fixed flow rates can produced with the vascular bypass graft of proper fixed flow rate selected for a particular patient prior to surgical placement. This embodiment reduces manufacturing complexity and cost while maintaining the vascular bypass graft's resistance to occlusion by clotting.

It will be understood that the above described arrangements of apparatus and the method therefrom are merely illustrative of applications of the principles of this invention and many other embodiments and modifications may be made without departing from the spirit and scope of the invention as defined in the claims.

What is claimed is:

1. An improved vascular bypass graft comprising:
 a primary bypass fabricated from a substantially hollow member defined by a primary bypass wall, the graft having a proximal vascular bypass end and a distal vascular bypass end, the proximal vascular bypass end configured to attach to a first vessel at a first point and the distal vascular bypass end configured to attach to the first vessel at a second point to bypass blood flow at a section of the first vessel, wherein the blood flow enters the primary bypass at the proximal vascular bypass end and exits the primary bypass at the distal vascular bypass end; and
 a venous outflow limb fabricated from a substantially hollow member, the venous outflow limb having a proximal venous end and a distal venous end, wherein the distal venous end is attached to and extends outward from the primary bypass wall at the distal vascular bypass end of the primary bypass to form a fluid pathway therebetween, the proximal venous end configured to attach to a second vessel having a lower pressure than the first vessel, the venous outflow limb also including a stenosis restrictor formed within the venous outflow limb, such that the stenosis restrictor is configured to control fluid flow through the venous outflow limb, and the venous outflow limb is configured to divert at least a portion of the blood flow through the primary bypass to the second vessel to maintain a blood flow within the vascular bypass graft to prevent clotting.

2. The vascular bypass graft of claim 1 wherein the proximal venous end is substantially configured as a diffuser, the proximal venous end flared outward to form the diffuser.

3. The vascular bypass graft of claim 1 wherein the venous outflow limb is integrally formed with the vascular bypass graft.

4. The vascular bypass graft of claim 1, wherein the stenosis restrictor is located adjacent to the proximal venous end.

5. The vascular bypass graft of claim 1, wherein the stenosis restrictor comprises a fixed flow rate.

6. The vascular bypass graft of claim 1 further comprising a restrictor controller operatively coupled with the stenosis restrictor.

7. The vascular bypass graft of claim 6, wherein the restrictor controller is operatively coupled with one or more sensors, the sensors configured to monitor one or more fluid dynamic parameters within the vascular bypass graft.

8. The vascular bypass graft of claim 6, wherein the controller is operatively coupled with an external control device, thereby forming an open-loop feedback control system.

9. The vascular bypass graft of claim 8, wherein the controller is wirelessly coupled with the external control device.

10. A method for adjusting the fluid flow through a vascular bypass graft comprising:
 monitoring at least one fluid dynamic parameter within the vascular bypass graft, the vascular bypass graft comprising:
  a primary member comprising a primary member wall, an inflow end, and an outflow end, wherein blood flow from a first vessel enters the primary member at the inflow end and exits the primary member at the outflow end; and
  a secondary member having a first end and a second end, the first end attached to and extending outward from the primary member wall at the outflow end of the primary member to form a fluid pathway between the primary member and the secondary member, wherein at least a portion of the blood flow through the primary member is diverted to a second vessel through the secondary member;
 accepting blood flow from a first vessel into the inflow end of the primary member from the first vessel;
 routing the blood through the primary member toward the outflow end;
 passing a first portion of the blood flow out the outflow end to the first vessel;
 passing a second portion of the blood flow from the primary member to the secondary member, the secondary member not connecting to the first vessel, wherein the second portion of the flow travels through the secondary member to a second vessel;
 determining one or more fluid flow conditions through the vascular bypass graft based on the at least one fluid dynamic parameter; and
 modifying a stenosis restrictor within the secondary member to adjust the pressure at the outflow end of the primary member to be greater than the pressure within the secondary member to maintain a blood flow within the vascular bypass graft that prevents clotting.

11. The method of claim 10, wherein the steps of monitoring and modifying are performed continuously.

12. The method of claim 10, wherein the step of modifying the stenosis restrictor is performed at one or more predefined timed intervals.

13. An improved vascular bypass graft comprising:
- a primary member, the primary member fabricated from a substantially hollow structure, the primary member having an inflow end and an outflow end wherein the inflow end and the outflow end are configured to connect to a first blood vessel to provide a blood flow path out of and into the first blood vessel; and
- a secondary member, the secondary member fabricated from a substantially hollow structure that includes a stenosis restrictor formed within the secondary member, such that the stenosis restrictor controls fluid flow through said secondary member, the secondary member having a first end and a second end, the first end attached to and extending outward from a wall of the primary member at the outflow end of the primary member to form a fluid pathway there between and the second end configured to connect to a second blood vessel to provide a blood flow path into or out of the second blood vessel;
- wherein the secondary member is configured to accept at least a portion of the blood flow through the wall of the primary member at the outflow end of the primary member directly into the secondary member to thereby maintain a blood flow within the vascular bypass graft even if the outflow end of the primary member were blocked to prevent clotting of the primary member.

14. The vascular bypass graft of claim 13 wherein the second end of said secondary member is substantially configured as a diffuser, the second end flared outward to form the diffuser.

15. The vascular bypass graft of claim 13 wherein the secondary member is integrally formed with said primary member.

16. The vascular bypass graft of claim 13, wherein the stenosis restrictor is located adjacent to said second end of said secondary member.

17. The vascular bypass graft of claim 13, wherein the stenosis restrictor comprises a fixed flow rate.

18. The vascular bypass graft of claim 13, further comprising a restrictor controller operatively coupled with the stenosis restrictor.

19. The vascular bypass graft of claim 18, wherein the restrictor controller is a controller operatively coupled with one or more sensors, the sensors configured to monitor one or more fluid dynamic parameters within the vascular bypass graft.

20. The vascular bypass graft of claim 19, wherein the controller is operatively coupled with an external control device, thereby forming an open-loop feedback control system.

21. The vascular bypass graft of claim 20, wherein the controller is wirelessly coupled with the external computer.

22. A method for surgically implanting a vascular bypass graft comprising:
- inserting an vascular bypass graft adjacent a vascular occlusion of a first vessel, wherein said vascular bypass graft comprises:
  - a primary bypass fabricated from a substantially hollow member, the graft having a proximal vascular bypass end and a distal vascular bypass end, wherein the blood flow enters the primary bypass at the proximal vascular bypass end and exits the primary bypass at the distal vascular bypass end; and
  - a venous outflow limb fabricated from a substantially hollow member, the limb having a proximal venous end and a distal venous end, the distal venous end attached to and extending from a wall of the primary bypass at the distal vascular bypass end of the primary bypass to form a fluid pathway between the primary bypass and the venous outflow limb;
- connecting the proximal vascular bypass end of the primary bypass to the first vessel at a point upstream from the vascular occlusion of the first vessel;
- connecting the distal vascular bypass end of the primary bypass to the first vessel at a point downstream from the vascular occlusion of the first vessel; and
- connecting the proximal venous end of the venous outflow limb to a second vessel having lower pressure than the first vessel, wherein the venous outflow limb is configured to divert at least a portion of the blood flow through the wall of the primary bypass into the venous outflow limb and then into the second vessel to thereby maintain a blood flow within the vascular bypass graft that prevents clotting.

23. The method for surgically implanting a vascular bypass graft of claim 22 wherein said vascular bypass graft further comprises:
- a stenosis restrictor formed within the venous outflow limb and adjacent to the proximal venous end, wherein the stenosis restrictor controls fluid flow through the venous outflow limb.

* * * * *